United States Patent [19]

Nowacki et al.

[11] Patent Number: 4,598,279

[45] Date of Patent: Jul. 1, 1986

[54] PRESSURE MONITOR

[75] Inventors: Christopher Nowacki, Arlington Heights; Alfred G. Brisson, Schaumburg, both of Ill.

[73] Assignee: Trutek Research, Inc., Arlington Hts., Ill.

[21] Appl. No.: 541,686

[22] Filed: Oct. 13, 1983

[51] Int. Cl.<sup>4</sup> ...................... G08B 21/00; A61M 16/00
[52] U.S. Cl. ................. 340/626; 128/202.22; 128/204.21
[58] Field of Search ....................... 340/626, 611, 614; 200/83 C, 83 N, 81.4, 83 R; 128/202.22, 205.23, 204.28, 204.23

[56] References Cited

U.S. PATENT DOCUMENTS 3,333,584 8/1967 Andreasen et al. .............. 340/611 X Primary Examiner—James L. Rowland
Assistant Examiner—Anne Marie F. Capati
Attorney, Agent, or Firm—Trexler, Bushnell & Wolters, Ltd.

[57] ABSTRACT

A pressure monitor is provided for gas pressure supplied to a patient. The monitor includes a pair of spaced contacts in the form of crank arms. A spring member is fixed at one end and is deflectable by a pneumatic cushion supplied with air from the gas supplied to a patient. The pneumatic cushion interacts with the resiliency of the spring member to urge the spring member to an intermediate position between a pair of fixed contacts. Too low a gas pressure will permit the spring member to engage one contact, while too high a gas pressure will cause the spring member to engage the other contact. Closure of the spring member against either contact energizes a respective alarm. In addition, there is provided a preset pneumatic-electrical switch connected to an oxygen supply line to indicate low oxygen pressure.

6 Claims, 8 Drawing Figures

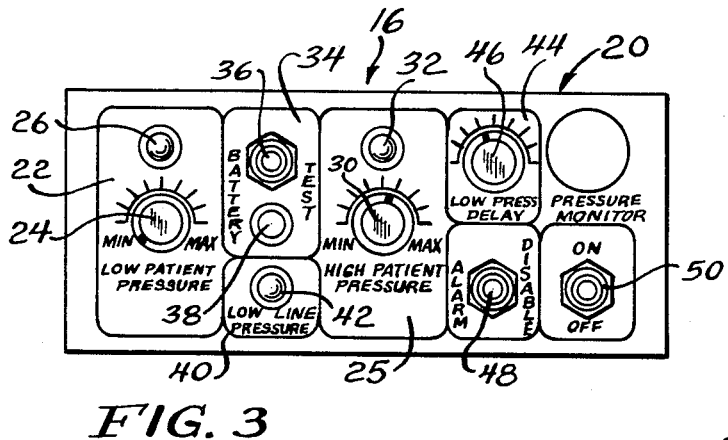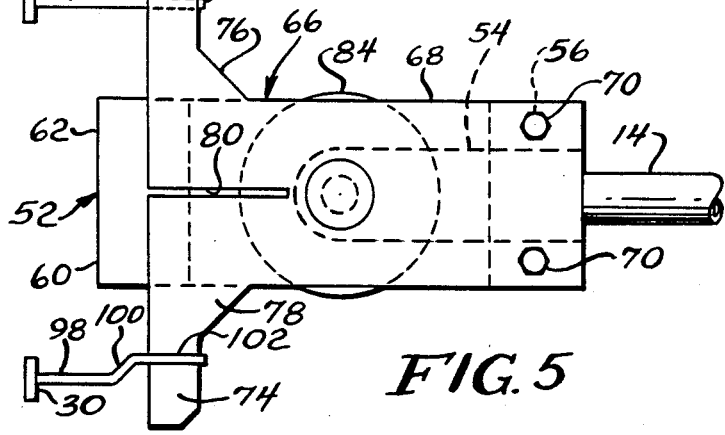

PRESSURE MONITOR

BACKGROUND OF THE INVENTION

Gasses for inhalation are provided to medical patients under at least two totally different conditions. Anesthesiology gasses are applied during surgery, either through a mask, or through an endotracheal tube. Oxygen or a mixture of air and oxygen is supplied to a patient when the patient has trouble breathing on his own. In either case it is imperative that the pressure of the gasses supplied to the patient be within a certain range, neither too low nor too high.

OBJECTS AND SUMMARY OF THE PRESENT INVENTION

It is an object of the present invention to provide a pressure monitor connected to the patient ventilator and having adjustable controls thereon for providing an alarm if the pressure drops below a predetermined minimum or rises above a predetermined maximum.

It is a further object of the present invention to provide a pressure monitor of simple and inexpensive construction for connection to a patient ventilating circuit and adjustably operable to provide an alarm signal if the pressure drops below a desirable minimum or rises above a desirable maximum.

In achieving the foregoing and other objects we have provided a pressure monitor connected to a patient ventilating circuit by a simple T connector to indicate if the ventilator is operating or not. The line connected by the T connector is connected to a bellows device bearing against a metallic spring member. The bellows device raises the spring member, or permits it to lower, depending on the pressure in the line. If the pressure becomes too great the spring member is raised to a predetermined level and completes an electrical contact to sound an alarm. Conversely, if the pressure drops below a predetermined minimum, the bellows device collapses sufficiently that the metallic spring member contacts a second electrical contact. It does so drop on each exhalation, and a time delay circuit is enclosed so that if the spring member contacts the second contact more than a predetermined time a circuit is completed to operate an alarm indicating the pressure to be too low. Both the high pressure and low pressure limits are adjustable. The alarm can be disabled when it is desired to suction a patient, or for other purposes, and an adjustable time delay is provided so that the alarm might be energized immediately, or after a desired delay of up to approximately 60 seconds.

DRAWING DESCRIPTION

FIG. 1 is a schematic circuit illustrating connection of the pressure monitor to the patient ventilating circuit;

FIG. 2 is a schematic diagram showing operation of the patient monitor;

FIG. 3 is a view of the front panel of the pressure monitor;

FIG. 4 is a side view partly in section of the pressure responsive bellows device and the electrical contacts operated thereby;

FIG. 5 is a top view of the structure of FIG. 4;

FIG. 6 is a detail sectional view illustrating the adjustable feature of the high and low limit pressure contacts;

FIG. 7 is a schematic diagram of a circuit to indicate the low line pressure; and FIG. 8 is a schematic diagram illustrating another safety alarm feature of the invention.

DETAILED DISCLOSURE OF THE ILLUSTRATED EMBODIMENT

A schematic illustration of the utilization of the present invention is shown in FIG. 1. A pneumatic tube or line 10 leads from a gas source to a T fitting 12 which is in turn connected straight-through to a line or pneumatic tubing 13 leading to a patient. The gas source may be an anesthesiology gas, generally mixed with air or oxygen, or it may be oxygen, either pure or mixed with air. The stem of the T fitting 12 is connected through a line or pneumatic tubing 14 to the pressure monitor 16 forming the subject matter of the present invention. An oxygen line 18 also is connected to the pressure monitor as will be brought out hereinafter. The gas sources are rather low pressure, and the pneumatic tubings 10, 13, and 14 generally comprise plastic tubings which are connected to the T fitting 12 by a tight fit. The T may be either male or female, but in general is a male-type fitting so that it somewhat stretches the plastic of the tubing.

The pressure monitor 16 has a plurality of functions as may be understood from reference to the front panel 20 thereof in FIG. 3. At the left side there is a panel section 22 relating to low patient pressure, and a knob 24 thereon is rotatable to set a desirable limit to minimum pressure. If the pressure drops below the preset amount the pressure monitor will cause an audible alarm to sound, and will cause a red light 26 to become energized. For low current consumption this is preferably a light emitting diode, but other light sources including incandescent could be used. Typically the low pressure limit is set in the area of 0 to 50 cm. of water. Spaced somewhat to the right there is a high pressure face plate or lable area 25 similar to the low pressure area 22 and having a knob 30 for adjustably setting the desired high pressure limit. If the pressure in the line 14 exceeds the high pressure limit as set then an audible alarm will sound and a light 32 will be energized. As with the low pressure light this may be a light emitting diode, an incandescent lamp or other.

Intermediate the low patient pressure and high patient pressure areas there is a battery test area 34 including a push-button switch 36 and a light source 38 that is energized if the battery is of sufficient potential. This light source again can be a light emitting diode, but could also be an incandescent lamp or otherwise. Immediately below the battery test area, there is a low line pressure area 40 having a light source 42 thereon, again preferably a light emitting diode, although other light sources including incandescent are within the contemplation of the present invention. The low line pressure light source is connected to a preset switch which is incorporated in a pneumatic device in the pressure monitor which is connected to the oxygen line 18. Typically a hospital will have a master oxygen line in areas in which oxygen will be used, and the oxygen is rather uniformly supplied at 50 PSI. The pneumatically operated switch is factory preset at 40 lbs. per square inch, and if the pressure drops below 40 lbs., then the switch closes to sound an audible alarm and also to energize the light source 42. Usually the pressure would drop in this manner in the event of an accidental disconnection of the oxygen source, usually a pressure tank, or exhaustion of the oxygen supply.

To the right of the high patient pressure area, there is a low pressure delay area 44 having a rotatable knob 46. This and the two previously mentioned knobs are provided with pointers and scales as will be apparent. This knob adjusts an electrical delay device so that there is an adjustable time delay from the first instant when line oxygen pressure drops below 40 lbs. per square inch. It is entirely possible that there could be fluctuating low pressure, and it is not necessary to respond if the line pressure drops for a matter of a few seconds.

Immediately below the low pressure delay area there is an alarm disable switch 48. When first setting up the pressure monitor, or if the ventilating device is removed from the patient's face as to suction mucus from the patient, it is not desired for the alarm to sound. Accordingly, this switch temporarily disables the alarm for a preset period of time.

Both the battery test switch 36 and the alarm disable switch 48 are push button switches which are closed only when manually depressed, and open upon release. To the right of the alarm disable switch there is an on/off toggle switch 50 which turns the pressure monitor on and off.

As may be seen in FIGS. 4 and 5 the pressure monitor is provided with a mounting block 52 having an elongated U shaped slot 54 extending longitudinally of the block and in the lower portion thereof. A transverse mounting member 56 forming an integral part of the block 52 overlies the slot 54. The block 52 has a recess 58 in the upper portion thereof separating the mounting member 56 from a like transverse platform section 60 having an upper surface 62 on the same level as the upper surface 64 of the transverse member or portion 56.

A somewhat T shaped metal spring 66 is mounted on top of the block 52. The spring has a relatively wide stem 68 with the extremity thereof secured to the block atop the transverse section 56 by means such as screws or bolts 70. The spring 66 has a low pressure arm 72 and a high pressure arm 74 extending from the end thereof opposite to the bolts 70, and this end normally lies on the surface 62, the spring initially being flat. The arms 72 and 74 are respectively gussetted at 76 and 78, respectively, to the stem 68. A longitudinal slit 80 is provided between the arms and in the stem 68 to permit a certain degree of resiliency of the arms 72 and 74 independently of one another. A pneumatic fitting is disposed in the slot or recess 54 and partially in the recess 58, and carries an expansible pneumatic member in the nature of a bellows 84. The fitting includes an enlarged circular member 86 lying in the recess 58 and extending slightly beyond the longitidinal edges of the block 52. This fitting has a pipe-like structure recessed in the upper surface thereof, (not shown) for receiving the bellows like device 84. On its lower portion the fitting 82 includes a pipe connector 88 on which the line or tubing 14 is secured, largely by friction fit, and partly through slight stretghing of the tubing. The pipe-like member is joined to the circular upper portion 86 by a circular body portion 90 of smaller diameter received in a slot or recess 54.

The block 52 and the fitting 82 are made of suitable plastic material, a molded acrylic resin being one suitable example. The bellows-like member 84 comprises a generally flat plastic pillow or cushion of suitable resilient plastic material such as polyethylene. The top surface thereof normally is flat, and the bottom surface is provided with a depending neck (not shown) which interfits with the upstanding pipe-like member in the upper portion 86 of the fitting 82. It is secured thereto by a stretch fit, and/or a suitable adhesive. The bellows-like member or cushion 84 underlies the stem of the spring 66 and in a totally relaxed state extends above the surfaces 62 and 64. However, the spring 66 tends to flatten the bellows device or cushion 84, and does flatten it to a greater or lesser extent depending on the gas pressure in the line 14. In FIG. 4, the spring is shown in a balanced condition where the pressure within the line 14 and within the cushion 84 holds the spring deflected upwardly in an intermediate position. The broken line position of the spring shown in FIG. 4 is the position that the spring tends to assume, but never actually reaches due to engagement with the crank arm 96 referred to hereinafter.

The low pressure knob 24 is fixed on the end of a shaft 92 which is rotatably mounted in a portion of the panel 20 as will be described shortly hereinafter. Interiorally or rearwardly of the panel the shaft is provided with an offset 94 which then continues as an arm 96 parallel to the shaft 92. The shaft 92, offset 94, and arm 96 effectively form a crank with the arm 96 underlying the spring arm 72. The vertical height of the arm 96 is adjustable by turning of the knob 24. If the spring lowers sufficiently against the cushion 84, then it contacts the crank arm 96 to complete an electric circuit as will be set forth shortly hereinafter.

Similarly, the knob 30 is fixed on a shaft 98 having an offset 100 leading to an arm 102, the whole forming a crank. The crank arm 102 overlies the spring arm 74, and is vertically adjustable by turning of the knob 30. If the cushion 84 expands sufficiently under gas pressure to raise the spring 66 and specifically the arm 74 thereof into contact with the crank arm 102, an electric circuit will be completed as will be set forth shortly hereinafter.

It will be appreciated that it is undesirable for either of the cranks just described to turn inadvertently as this would vary the desired minimum and maximum pressures. Accordingly, we provide structure for preventing this as shown in FIG. 6. In this figure the knob 24 for low patient pressure is shown mounted on the shaft 92, having the offset 94 and crank arm 96. The shaft is rotatable in the front panel 20 and also in a cup-shaped member 104 suitably secured on the back face of the panel. The cup shaped member has an end wall 106 which is provided with an aperture 108 having internal teeth or serrations. A gear member 110 is fixed on the shaft 92 and is provided with external teeth or serrations which mesh with the internal teeth or serrations of the opening 108. A compression spring 112 seats against a flat plate or washer 114 on the inner surface of the wall 106, which plate also serves as a limit outwardly for the shaft 92 and knob 24. The opposite end of the spring may extend through the shaft 92 as indicated at 116. Thus, the gear 110 is normally held in the position in solid lines in FIG. 6 with external teeth or serrations thereon matching with the complementary internal teeth or serrations in the hole or opening 108. When it is desired to turn the knob the knob is pushed inwardly (toward the panel) which moves the gear 110 out of mesh with the teeth or serrations in the hole 108 as shown in dashed lines in FIG. 6. The knob then can be turned, and upon release of the knob the knob and shaft are returned to the solid line position by the spring 112, the teeth or serrations on the gear again meshing with the internal teeth or serrations in the hole 108 to prevent undesired turning or rotation of the knob and shaft.

Operation of the pressure monitor to the extent that it has heretofore been shown and described will be understood with reference to FIG. 2. The patient monitor is powered by a battery 118, conveniently a 9 volt transistor battery. The on/off switch 50 is preferably connected at one end or the other of the battery, being illustrated in the ground side or negative side thereof. The alarm disable including the switch 48 is illustrated at 125, also in the ground side of the battery circuit, although it could equally well be in the positive side. The alarm disable simply opens the series circuit of the battery for a sixty second period following pushing of the switch 48, and for example, may simply comprise a resistor-capacitor time delay circuit and a switch which is momentarily opened when the switch button 48 is depressed.

The battery test light source 38, illustrated as a light emitting diode, is shown as being connected to a junction 120 on the positive side of the battery and in series with the switch 36. The switch will be understood as being a momentary switch which is closed only when held in depressed position, and which opens immediately upon release. A resistor may be included in circuit with the light source if desired in order to load the battery.

The positive side of the battery further is connected through a wire 122 to the switch 66. The inherent resilient biasing of the switch along with the degree of inflation of the pneumatic cushion 84, depending on the pressure therein, effects centralization of the spring 66 as shown, or upward or downward movement respectively to engage the high pressure crank arm 102 or the low pressure crank arm 96 respectively to complete a circuit either through the low pressure alarm 124 (through the delay circuit 125) or the high pressure alarm 126. The spring always drops on exhalation so that the arm 72 contacts the crank arm 96. It is not desired that the alarm be energized unless this contact lasts longer than a predetermined time until the next inhalation. The delay circuit 125 thus delays the alarm. The low pressure alarm includes an audible alarm, which can be a buzzer, or a more modern electronic sound source. The low pressure alarm also includes the low pressure light 26 so that medical personnel in attendance can tell that it is the low pressure alarm. The high pressure alarm 126 also includes an audible alarm similar to that of the low pressure alarm, and further includes the light source 32 to indicate that it is the high pressure alarm that it sounding.

The high pressure alarm and the low pressure alarm are grounded on the opposite side to complete the electric circuit.

The line pressure alarm has previously been indicated as including a pneumatic switch, and this is shown at 128 in FIG. 7. The low pressure switch 128 is connected to the oxygen supply line 18, and since this is a fairly high pressure line it typically is a reinforced hose and is connected by threaded fittings. The low pressure switch is supplied with potential from a battery which may be and preferably is the aforementioned battery 118 and which may be connected through the same on/off switch 50. The positive side of the battery is connected direct to the low pressure switch 128, and this switch in turn is connected through wires 130 to the low pressure light source 42, and also to an audio alarm 132 in parallel therewith, and back to the switch 50. If the pressure in the oxygen supply line drops below the preset limit of 40 PSI the pneumatic-electric low pressure switch 128 is closed to sound the audio alarm 132 and simultaneously to energize the light source 42 to warn medical personnel present that the oxygen supply source has dropped in pressure, and that they should be prepared for a drop in the gas source pressure in the line 10 so that emergency measures may be taken as may be necessary.

A further safety feature is illustrated in FIG. 8. A second switch contact 50' gauged with the switch contact 50 is closed when the "on-off" switch 50 is open. One side of the switch contact 50' is connected to a pressure switch 133, and this is connected in turn to an alarm 134, the other side of which is connected to the terminal 120 at the positive terminal of the battery. The pressure switch is actuated by a branch 14' of the pressure line 14, easily constructed with a conventional T-connector. If the gas pressure is on and the switch 50 is not in the "on" position, a circuit will be completed through switch contact 50', pressure switch 132 and alarm 134 to cause the alarm to emit a constant audible signal, preferably accompanied by a red light.

The pressure monitor as herein shown and described is remarkably simple in construction, and hence of high reliability and low cost. The specific example will be understood as being exemplary. Various changes may occur to those skilled in the art and will be understood as forming a part of the present invention insofar as they fall within the spirit and scope of the appended claims.

The invention is claimed as follows:

1. A pressure monitor comprising base means, a contact member mounted on said base means and normally biased to a rest position, a pneumatic device on said base means adjacent said contact member and expansable in accordance with internal gas pressure against said contact member to move said contact member from rest position, means for connecting an external pneumatic line to said pneumatic device, the position of said contact member being determined by its resilient biasing and said internal gas pressure, a pair of electric contacts respectively engageable by said contact member as gas pressure increases or decreases beyond predetermined limits, high pressure and low pressure alarm means respectively connected to said pair of contacts and respectively energized when said contact member engages one of said pair of electrical contacts, means for respectively adjusting the position of said pair of contacts, the pair of contacts respectively comprising crank arms adjustable by rotation thereof.

2. A pressure monitor as set forth in claim 1 and further including means for respectively securing said pair of contacts against inadvertent movement.

3. A pressure monitor as set forth in claim 2 wherein the securing means comprises a rotary member having a predetermined external shape and selectively received in a hole of complementary shape in a fixed member.

4. A pressure monitor comprising base means, a contact member mounted on said base means and normally biased to rest position, a pneumatic device on said base means adjacent said contact member and expansable in accordance with internal gas pressure against said contact member to move said contact member from rest position, means for connecting an external pneumatic line to said pneumatic device, the position of said contact member being determined by its resilient biasing and said internal gas pressure, a pair of electric contacts respectively engageable by said contact member as gas pressure increases or decreases beyond predetermined limits, and high pressure and low pressure alarm means respectively connected to said pair of contacts and respectively energized when said contact member engages one of said pair of electrical contacts, said spring member comprising a T shaped leaf spring, having a stem fixed at one end for movement at the opposite end, and a pair of oppositely extending transverse arms at said other end and respectively engageable with said pair of contacts.

5. A pressure monitor as set forth in claim 4 wherein said pair of contacts respectively comprise crank members adjustable by rotation thereof.

6. A pressure monitor comprising base means, a contact member mounted on said base means and normally biased to a rest position, a pneumatic device on said base means adjacent said contact member and expansable in accordance with internal gas pressure against said contact member to move said contact member from rest position, means for connecting an external pneumatic line to said pneumatic device, the position of said contact member being determined by its resilient biasing and said internal gas pressure, a pair of electric contacts respectively engageable by said contact member as gas pressure increases or decreases beyond predetermined limits, and high pressure and low pressure alarm means respectively connected to said pair of contacts and respectively energized when said contact member engages one of said pair of electrical contacts, said spring member comprising a flat leaf spring, there being two spaced coplanar surfaces on said base means, said flat spring being fixed on one of said surfaces and resiliently tending to lie against the other thereof.

* * * * *